United States Patent [19]

Nakanishi et al.

[11] Patent Number: 4,776,335
[45] Date of Patent: Oct. 11, 1988

[54] LASER SPOT PROJECTOR

[75] Inventors: Takaji Nakanishi, Toyokawa, Japan; David R. Hennings, Half Moon Bay, Calif.; Masao Niino, Okazaki, Japan

[73] Assignees: Kowa Company Ltd., Aichi, Japan; Coherent Incorporated, Calif.

[21] Appl. No.: 919,319

[22] Filed: Oct. 14, 1986

[30] Foreign Application Priority Data

Oct. 18, 1985 [JP] Japan ................... 60-231316

[51] Int. Cl.$^4$ .............................. A61B 17/36
[52] U.S. Cl. .................... 128/303.1; 128/395
[58] Field of Search ........... 128/4, 6, 303.1, 395–398; 350/425, 429, 433, 559; 351/208; 219/121 LR

[56] References Cited

U.S. PATENT DOCUMENTS

| | | | |
|---|---|---|---|
| 4,397,310 | 8/1983 | Pomerantzeff | 128/395 |
| 4,520,816 | 1/1985 | Schacher et al. | 128/303.1 |
| 4,538,608 | 9/1985 | L'Esperance | 128/395 |
| 4,554,917 | 11/1985 | Tagron | 128/395 |
| 4,628,416 | 12/1986 | Dewey | 128/395 |

FOREIGN PATENT DOCUMENTS

| | | | |
|---|---|---|---|
| 0860192 | 1/1941 | France | 350/559 |
| 2441294 | 3/1975 | Fed. Rep. of Germany | 350/184 |

*Primary Examiner*—Max Hindenburg
*Attorney, Agent, or Firm*—Bruce L. Adams; Van C. Wilks

[57] ABSTRACT

Disclosed is a laser spot projector for use with a laser coagulation system in which a laser beam is radiated as a focussed spot into a portion selected to be thermally coagulated. A laser source produces a laser beam, and a focussing lens focusses the laser beam on the selected portion in the form of a focussed laser beam spot. A variator lens is displaceably arranged between the laser source and focussing lens for changing the magnification of the laser spot depending upon the displacement of the variator lens. The variator lens is selectably displaceable to two separate positions where the image point is conjugated with the object point with respect to the variator lens. This arrangement makes it possible to selectably provide two focussed laser beam spots each having a different spot diameter.

10 Claims, 4 Drawing Sheets

LASER SPOT PROJECTOR

BACKGROUND OF THE INVENTION

1. Field of the Invention

This invention relates to a laser spot projector, and more particularly to a laser spot projector for use with a laser coagulation system in which a laser beam is radiated as a spot into a portion selected to be thermally coagulated.

2. Description of the Prior Art

There have long been known laser coagulation systems in which during an ophthalmic operation against diseases such as retina detachment, glaucoma, etc., a patient's eye is irradiated with laser energy, which is absorbed by a biological organism such as retina to develop thermal coagulation thereon for ophthalmological treatment. For this purpose, the laser coagulation system includes a laser spot projector for producing a laser beam from an argon or krypton laser, which is condensed to a laser beam spot of a predetermined diameter, directed toward a predetermined portion of the eyeball to be coagulated, and then focussed thereon as a laser spot for thermally coagulating the portion selected.

The laser coagulation system further comprises a slit image projector for forming a slit image on the eyeball to illuminate the background and to define the predetermined portion of the eyeball to be coagulated, and an observation equipment for observing the slit image and laser spot in the eyeball.

In such an arrangement, the laser spot from the laser spot projector must be changed in diameter depending upon how large the portion to be coagulated is. To adjust the diameter of the laser spot, the laser spot projector is conventionally provided with a magnification changing device of a type which has already been used in the field of the laser beam machining.

However, such a laser spot projector in the prior art has the drawbacks that the magnification changing device is complicated in structure, not compact and very hard to operate.

SUMMARY OF THE INVENTION

It is therefore an object of the present invention to provide a laser spot projector capable of easily adjusting the magnification of the laser spot projected on the portion to be thermally coagulated.

It is another object of the present invention to provide a laser spot projector capable of being made compact, and easy to manufacture.

A laser spot projector according to the present invention comprises a laser source for producing a laser beam, a focussing lens for focussing the laser beam on a selected portion in the form of a laser spot, and a variator lens displaceably arranged between the laser source and focussing lens for changing the magnification of the laser spot depending upon the displacement thereof. The variatior lens is displaceable to a position such that object and image points of the variator lens lie at its conjugate points.

The variator lens is thus displaceable to a first position where a laser beam aperture at the object point is focussed to form the aperture image at the image point corresponding to one of the conjugate points of the variator lens, thus forming a laser spot having a first diameter. The variator lens is also displaceable to a second position such that the conjugate point at which the image point lies is reversed to an object point of the variator lens. Accordingly a laser spot having a second diameter different from the first diameter can be formed at the same image point. Thus, the laser spot projector of the present invention makes it possible to provide two sizes of focussed laser spot each having a different spot diameter.

According to the preferred embodiment of the present invention, the variator lens is further displaceable to a position where the object or image point of the variator lens lies out of the conjugate points. In this position, the laser spot can be adjusted to any magnification although the laser spot is not focussed.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
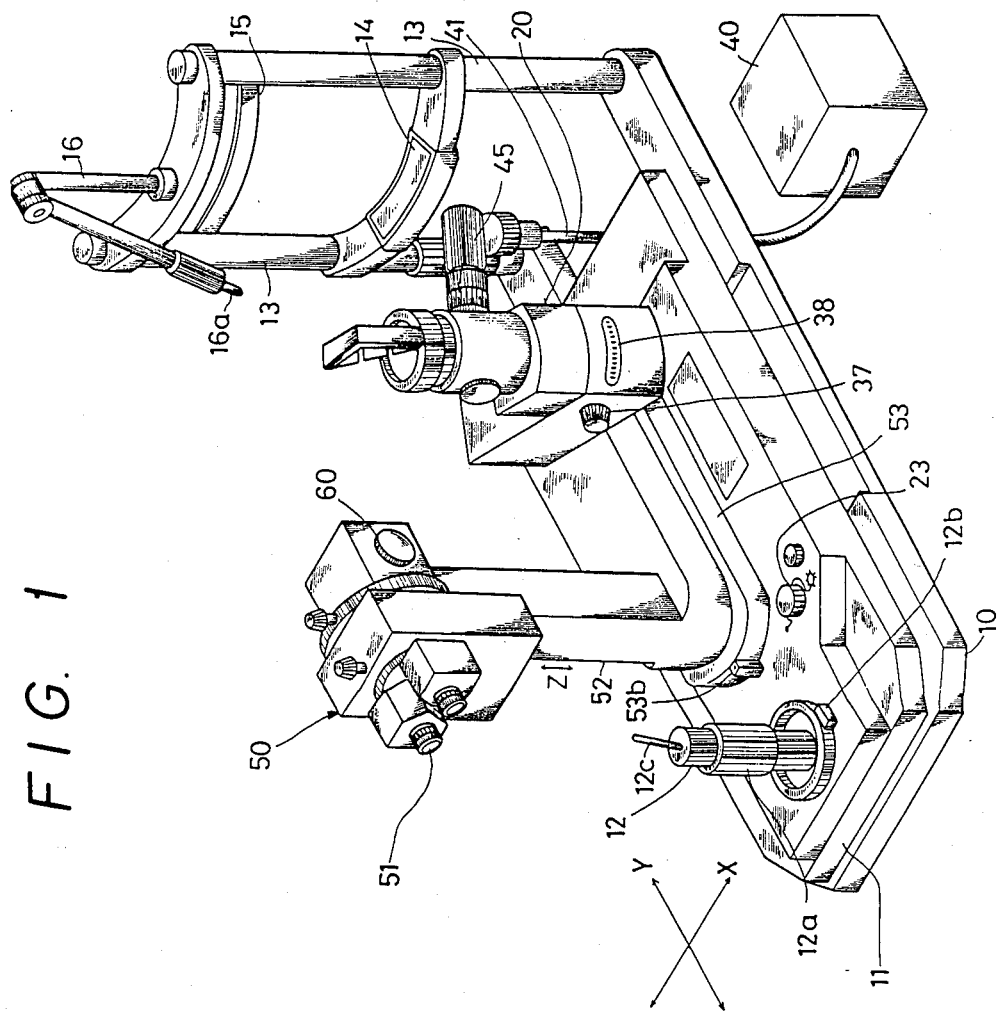
FIG. 1 is a perspective view showing a whole appearance of a laser coagulation system of the present invention.

FIG. 1 shows the appearance of a laser coagulation system including a laser spot projector according to the present invention. The laser coagulation system 1 includes a slider 11 mounted on a base plate 10 so as to be slidable relative to the base plate 10 in a direction X or Y by means of a manipulator 12 such as a joy stick. The displacement of the slider 11 relative to the base plate 10 can be effected by operating the manipulator 12 in the directions X and Y. The slider 11 supports thereon an instrument base 53 on which a slit image projector 20, a laser spot projector 21 and an observation equipment 50 are mounted as will be fully described later. The manipulator 12 is further provided with a handle 12a, the rotation of which allows the instrument base 53 to move upwardly or downwardly to displace the projectors 20 and 21 together with the observation equipment 50 vertically. Thus, the manipulator 12 can adjust the position of the instrument base 53 in the directions X and Y and in the vertical direction. The thus adjusted slider 11 can be locked on the base plate 10 by means of a lock 12b.

The base plate 10 has on its front edge two poles 13 between which a chin support 14 and a forehead pad 15 are fixedly mounted. A patient sits down in front of the apparatus with his chin on the support 14 and his forehead against the pad 15 and watches an eye fixation lamp 16a which serves to fix the patient's eye during measurement or coagulation.

Mounted on the rear end of the slider 11 is the slit image projector 20 which is turnable about the axis A (see FIG. 2) and serves to project a slit image onto the eyeball to illuminate the background and determine the portion of the eye to be measured or coagulated. As will be described later, the slit image projector 20 is arranged coaxially with the laser spot projector 21 for projecting a laser beam from a source 40 such as an argon or krypton laser through an optical fiber 41 onto that portion to be coagulated in the eyeball. The observation equipment 50 for observing the focussed laser spot or imaged slit in the eyeball is further arranged on the front edge of the slider 11 so as to be rotatable about the same axis as the turning axis A for the slit image projector 20.

Figure 2:
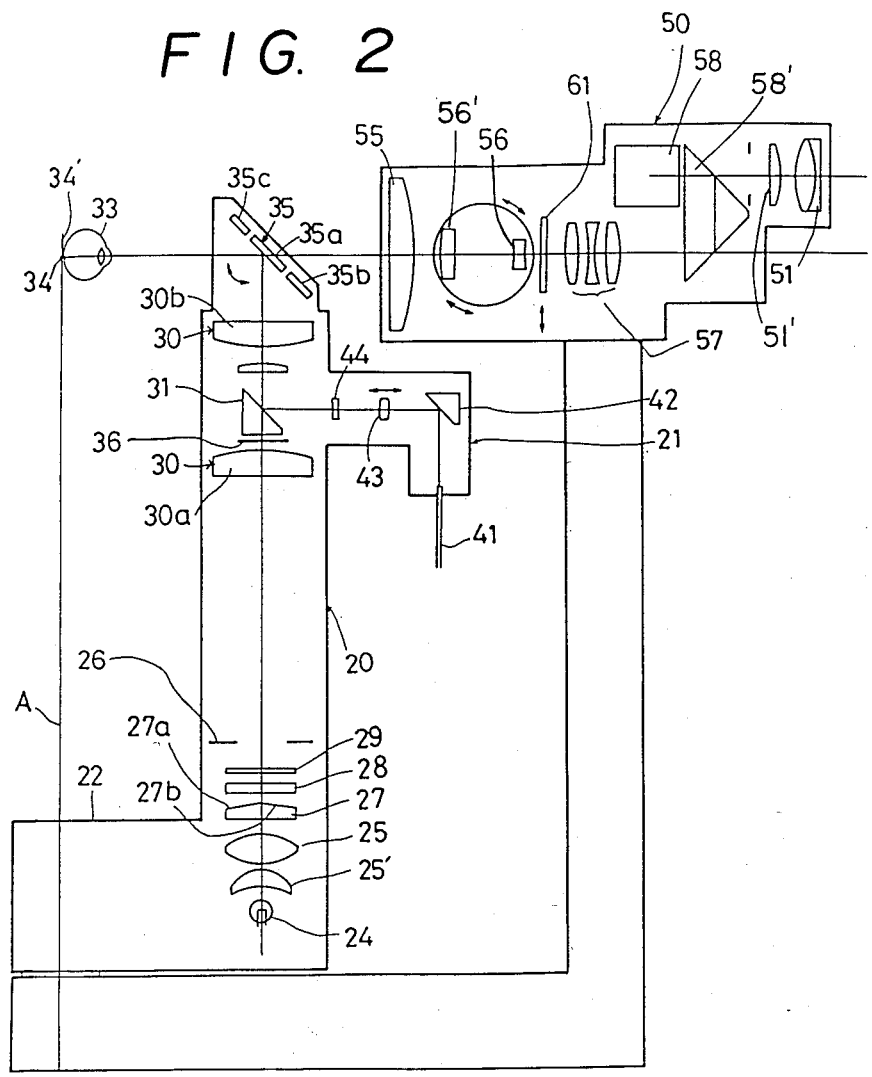
FIG. 2 is an illustrative view showing the arrangement of an optical system for a laser spot projector, slit image projector and observation equipment used in the laser coagulation system of the present invention.
Figure 3:
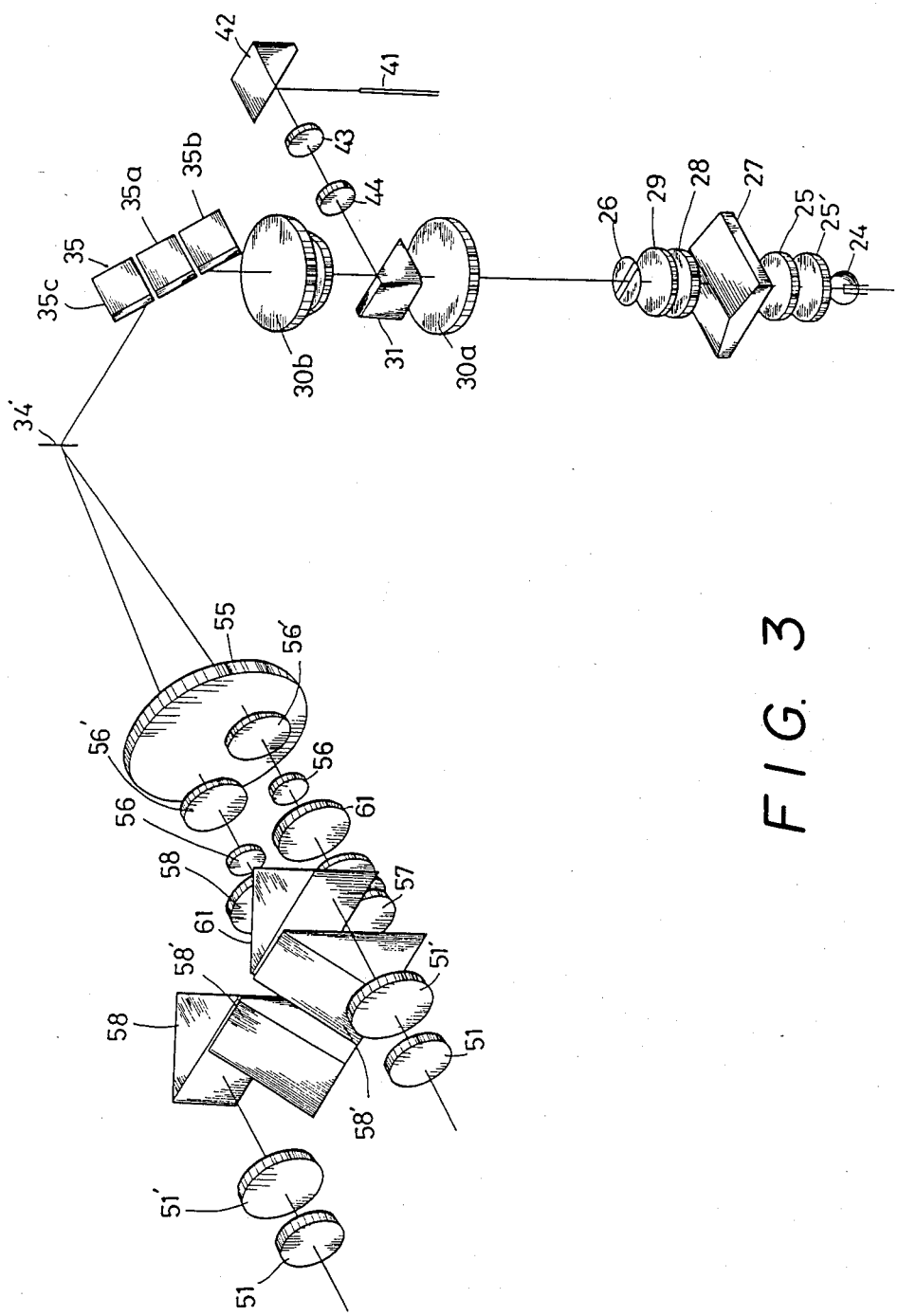
FIG. 3 is a perspective view showing the arrangement of the optical system in FIG. 2.

FIGS. 2 and 3 show the detailed arrangement of an optical system for the laser spot projector 21, slit image projector 20 and observation equipment 50. The slit image projector 20 is arranged in a housing 22 mounted so as to be rotatable about the axis A and is provided therein with a lamp 24 which is adjustable in intensity by means of an adjusting knob 23 (see FIG. 1). The lamp 24 emits illuminating light, which is converged by condenser lenses 25 and 25' to illuminate a slit aperture 26. Arranged between the condenser lens 25 and slit aperture 26 are a roof-shaped prism 27, an infrared ray cutting filter 28 and a detachable blue filter 29. The illuminated slit aperture 26 is imaged, for example, onto a retain 34 of a patient's eye 33 as a slit image 34' by means of a focussing lens 30 including lenses 30a and 30b. To eliminate the imaging function of the eye itself, a special contact lens(not shown) is attached to the patient's eye. A mirror assembly 35 having three-divided mirror portions 35a to 35c is mounted between the patient's eye 33 and lens 30b. The central mirror portion 35b can, as described later, be turned upwardly, downwardly, leftwardly or rightwardly about an axis perpendicular to or lying on the paper surface (in FIG. 2) by means of an operating lever 12c of the manipulator 12.

Arranged between the lens 30a and a prism 31 is a screen plate 36 which serves to interrupt the arrival of slit light to the central mirror 35a, while permitting it to reach the upper and lower mirrors 35b, 35c to the retina 34. To make the slit image on the retina 34 brighter and sharper, the deflection prism 27 has one surface 27a angled to deflect light toward the lower mirror 35b and the other surface 27b also angled to deflect light toward the upper mirror 35c. Thus, the deflection prism 27 functions to form the filament image of the lamp 24 at two points existing on the entrance pupil of the focussing lens 30.

It is to be noted that the slit width and length of the slit aperture 26 are adjustable by adjusting knobs 37 and 38 and the intensity of the lamp 24 are adjustable by an adjusting knob 23.

The laser spot projector 21 is, on the other hand, arranged in the same housing 22 as the slit image projector 20. The laser beam passing through the optical fiber 41 from the laser source 40 is deflected rectangularly at a prism 42 toward a variator lens 43 and a lens 44, reflected at the prism 31 and then advanced along the same optical path as the slit image projector 20 through the lens 30b, mirror 35a and the contact lens (not shown) to radiate the laser spot of a predetermined diameter on the retina 34 for thermal coagulation. The spot diameter of the laser beam can be adjusted in the range of about 50 $\mu$m to 1 mm by turning a knob 45 and adjusting the variator lens 43.

The instrument base 53 (FIG. 1) is provided with the housing 22 for accommodating the projectors 20 and 21 and a housing 52 for accommodating the observation equipment 50, and is displaceable vertically by using the handle 12a of the manipulator 12 as mentioned before. Further, the housings 22 and 52 are turnable to each other about the axis A, so that the projectors 20, 21 and the observation equipment 50 can undergo upward, downward or turning movement, respectively. The observation equipment 50 includes an optical system comprised of an objective lens 55, variator lenses 56 and 56', a safety filter 61, a focussing lens 57, erecting prisms 58 and 58', and eyepieces 51, 51'. The observation equipment 50 allows the observation of the slit image and laser spot formed in the eyeball. The adjustment of a knob 60 causes the variator lens 56 to be adjusted to provide an enlarged or reduced slit image or laser spot. The safety filter 61 is used to interrupt the laser beam reflected back from the irradiated portion of eye or cornea and to protect the eyes of an observer. For this purpose, the safety filter 61 is automatically inserted into the optical path of the observation equipment 50 immediately before the laser source 40 is activated to produce a stronger laser beam.

It should be noted that the optical elements following the objective lens 55 are provided in pairs respectively to allow binocular observation.

FIGS. 4 to 7 show a main portion of the laser spot projector 21.

For an optical system where a laser beam emitted from an aperture of the optical fiber 41 disposed at a point A is repeatedly reflected or refracted and focussed to form an aperture image at a point A', the point A is commonly designated as an object point and the point A' as an image point. If the laser beam or light is caused to advance reversely from the image point A', then the light is focussed on the object point A. In this case, the point A serves as the image point and the point A' as the object point, so that the object and image points are exchangeable in its function. It this connection, a pair of object and image points are called conjugate points, respectively.

Figure 4:
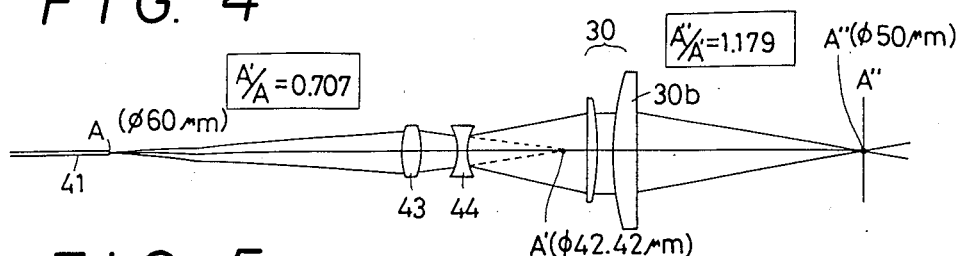
FIGS. 4 to 7 are illustrative views each showing how the laser beam can be focussed depending upon the position of a variator lens used in the laser spot projector of the invention.
Figure 5:
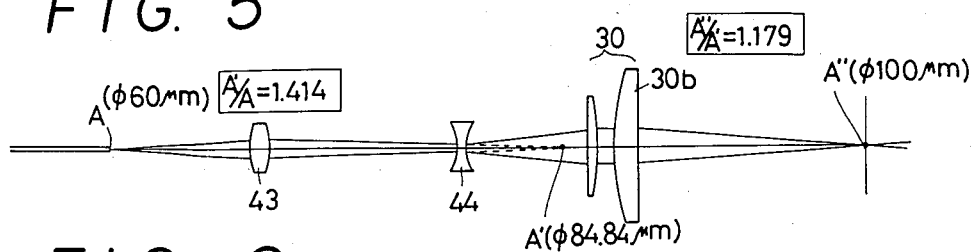

In the case of the embodiment in FIG. 4, the top edge of the fiber 41 forms the aperture disposed at the object point to form an aperture image with respect to the image forming means in the form of a variator lens 43, and a point A' at which an aperture image is formed is the image point measured from the variator lens 43. Thus, the distance between the points A and A' is kept the same even if the variator lens 43 is selectably displaced from one position to the other separate position to have its conjugate points reversed, for example, as shown in FIG. 5.

Now assume that a point A" is a focal point which exists on the retina and coincides with a treatment point and on which the aperture image is focussed by the focussing lens 44 and 30 through the variator lens 43. When the variator lens 43 is placed in one specific position as shown in FIG. 4, the magnification rate of the variator lens 43 is calculated as A'/A=0.707. Accordingly, the aperture A of 60 $\mu$m diameter at the object point A is imaged by the variator lens 43 to form the aperture image having a reduced diameter of 42.42 $\mu$m at the image point A'. The focussing lenses 44 and 30 are disposed between the image point A' and a treatment point A" to determine the magnification rate thereof A"/A'=1.179 and then causes the formation of a focussed aperture image having a diameter of 50$\mu$um at the treatment point If, on the other hand, the variator lens 43 is shifted toward the object point A as shown in FIG. 5 in the reversed position with respect to the object and image points A and A' as shown in FIG. 5, then the magnification rate of the variator lens 43 A'/A is equal to 1.414. Accordingly, the variator lens 43 forms the aperture image of 84.84 μm diameter at the common image point A' and a laser beam spot having a diameter of 100 μm on is focused the treatment point A". Since the focussing lenses 44 and 30 has the same magnification rate $A''/A' = 1.179$.

Thus, the utilization of the conjugated relation between the object and image points in the optical system allows the formation of a focussed clear spot image.

Figure 6:
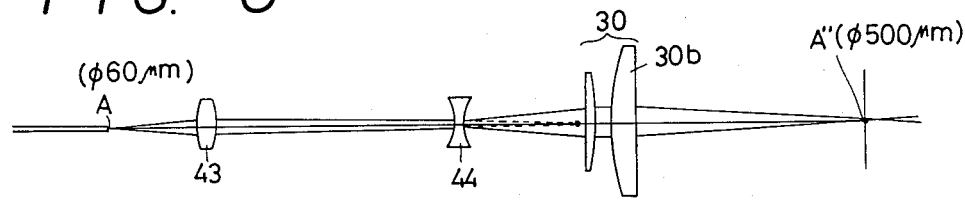
Figure 7:
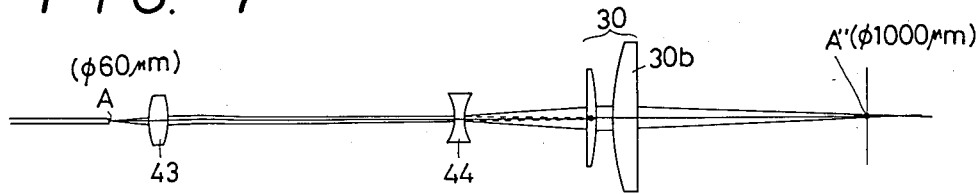

If the variator lens 43 is further displaced toward the object point A out of its conjugation, then the spot image on the treatment point A" becomes blurred or defocussed and has a diameter of 500 μm or 1000 μm, for example, as shown in FIGS. 6 and 7. This makes it possible to produce a spot image having any diameter, although it appears to be out of focus.

It is to be noted that an operating lever may be provided in the housing or lens barrel to displace or adjust the variator lens 43 in accordance with a scale provided thereon.

The operation of the laser coagulation system according to the present invention will now be described.

The patient first sits down with his chin on the support 14 and his forehead against the pad 15 and pays the watches the eye fixation lamp 16. The lamp 24 of the slit image projector 20 is then turned on to form the slit image 34' on the retina 34 of the patient's eye 33 through the contact lens set thereon. The slit light has its central flux inhibited to arrive at the central mirror 35a by means by the screen plate 36 and is reflected only at the upper and lower mirrors 35b and 35c to form the slit image 34' on the retina 34. In this case, the deflection prism 27 is used to deflect the slit light towards the mirrors 35b and 35c effectively. The intensity of the slit image can be adjusted by the knob 23, and the slit width and length can be adjusted by the adjusting knobs 37 and 38.

If the slit image 34' deviates from the desired place in the above-mentioned slit image formation, the manipulator 12 may be operated to displace the slider 11 and the housings 22 and 52 in the directions X, Y and Z and turn the projectors 20, 21 or observation equipment 50 about the axis A relative to each other until the slit image is formed on the desired portion for coagulation.

The thus formed slit image 34' can be observed by the optical system of the observation equipment including the objective lens 55, variator lens 56, imaging lens 57, erecting prism 58 and eyepiece 51. After the portion of eye to be coagulated has been determined, the laser source 40 is activated to emit a week laser beam, which is caused to pass through the prism 42, variator lens 43, lens 44, prism 31, and lens 30b, reflected at the central mirror 35a and then focussed as a spot onto the retina 34. For coagulation, a stronger laser beam is generated from the laser source 40 by changing power. When the stronger beam is activated, the safety filter is automatically inserted into the optical path of the observation equipment 50 to protect the eyes of the observer from the laser beam reflected from the irradiated portion of the patient's eye or retina.

For fine and precise coagulation the laser spot on the retina 34 can be displaced by scanning the central mirror 35a vertically or horizontally, that is, in the direction X or Y using the operating lever 12c of the manipulator 12.

The adjustment of the knob 45 allows the variator lens 43 to be displaced to adjust the spot diameter of the laser beam, as described in conjunction with FIGS. 4 to 7.

It will also appreciated that the variator lens 43 may comprise not only one lens, but also a plurality of lenses and/or reflecting means such as mirrors for deflecting the optical path.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for ophthalmic laser treatment of the eye of a patient, comprising: slit image projecting means for producing a slit of light and projecting a slit image into the eye of a patient to illuminate the eye to enable a determination as to the treatment portion of the eye to be treated, the slit image projecting means including a source of light, and means for forming the light from the light source into a slit image composed of two slit image components; laser beam projecting means for projecting a laser beam into the eye of the patient for treating the eye; wherein both the slit image projecting means and the laser beam projecting means include a common reflecting means for selectively reflecting the slit image and the laser beam toward the eye, the common reflecting means having two side portions positioned to reflect and direct the respective slit image components toward the eye to illuminate the eye to thereby determine the treatment portion, and a central portion positioned to reflect and direct the laser beam toward the determined treatment portion to treat the eye; and wherein the laser beam projecting means includes a laser source for producing the laser beam, a focussing lens for focussing the laser beam on the determined treatment portion of the eye in the form of a focussed laser spot, and a variator lens displaceably arranged between the laser source and focussing lens for changing the magnification of the focussed laser spot according to the position of the variator lens, the variator lens being displaceable to a first position such that its object point corresponds to one conjugate point of the variator lens and its image point corresponds to the other conjugate point thereof with the object and image points spaced apart a given axial distance from one another so that the focussing lens forms a first focussed laser spot on the determined treatment portion, and being displaceable to a second position such that its object point corresponds to the other conjugate point and its image point corresponds to said one conjugate point while maintaining the given axial distance between the object and image points so that the focussing lens forms on the determined treatment portion a second focussed laser spot having a spot diameter different from that of the first focussed laser spot.

2. An apparatus according to claim 1; wherein the laser beam projecting means includes means for holding the focussing lens at a fixed distance with respect to the determined treatment portion of the eye.

3. An apparatus according to claim 1; wherein the slit image projecting means includes a condenser lens for condensing the light from the source of light, and a deflection prism arranged between the condenser lens and the means for forming the slit image and having a roof-shaped surface, one half of which serves to deflect the condensed light toward one side portion of the common reflecting means through the means for forming the slit image, and the other half of which serves to deflect the condensed light toward the other side portion of the common reflecting means through the means for forming the slit image.

4. A laser spot projector for use with a laser coagulation system in which a laser beam is radiated as a spot onto a selected portion of an area to be thermally coagulated, the laser spot projector comprising:
   a laser source for producing a laser beam;
   a focussing lens for focussing said laser beam on a selected portion of an area in the form of a laser spot; and
   a variator lens displaceably arranged between said laser source and focussing lens for changing the magnification of said laser spot according to the position of the variator lens, said variator lens being displaceable to a first position such that its object point corresponds to one conjungate point of said variator lens and its image point corresponds to the other conjugate point thereof with the object and image points spaced apart a given axial distance from one another so that the focussing lens forms a first focussed laser spot on said selected portion, and being displaceable to a second position such that its object point corresponds to the other conjugate point and its image point corresponds to said one conjugate point while maintaining the given axial distance between the object and image points so that the focussing lens forms a second focussed laser spot having a spot diameter different from that of said first focussed laser spot.

5. A laser spot projector according to claim 4 including means for holding said focussing lens at a fixed distance with respect to the position of said selected portion.

6. An apparatus for directing a laser beam along an optical axis to a treatment point for use during a surgical operation, comprising: emitting means having means defining an aperture disposed at a definite object point on an optical axis for emitting a laser beam from the aperture along the optical axis; image forming means selectively displaceable along the optical axis to one of two selected positions for selectively forming two aperture images different in size according to the selected position of the image forming means at a common image point conjugated with the object point with respect to the image forming means to thereby maintain the axial distances between the aperture and one of the two aperture images and between the aperture and the other of the two aperture images equal to each other; and focussing means disposed between the common image point and the treatment point on the optical axis for focussing the aperture image selectively formed at the common image point onto the treatment point to form thereon a corresponding focussed aperture image so that the laser beam travelling along the optical axis is irradiated onto the treatment point in the form of a focussed spot which corresponds to the focussed aperture image and which has a size determined according to the selected position of the image forming means.

7. An apparatus according to claim 6 wherein the emitting means includes an optical fiber for transmitting therethrough the laser beam, the optical fiber having a top edge defining an aperture for emitting therefrom the transmitted laser beam.

8. An apparatus according to claim 6 wherein the image forming means comprises a variator lens operative when placed in one of the two selected positions to form an enlarged aperture image and operative when placed in the other selected position to form a reduced aperture image.

9. An apparatus according to claim 8 wherein the focussing means comprises an objective lens for magnifying the enlarged and reduced aperture images with the same rate.

10. An apparatus according to claim 9 wherein the objective lens is positioned a fixed distance from the treatment point.

* * * * *